United States Patent
Murakami et al.

(10) Patent No.: US 7,931,610 B2
(45) Date of Patent: Apr. 26, 2011

(54) BLOOD PURIFICATION APPARATUS

(75) Inventors: Tomoya Murakami, Shizuoka (JP);
Masahiro Toyoda, Shizuoka (JP); Akari Agata, Shizuoka (JP)

(73) Assignee: Nikkiso Co., Ltd., Tokyo (JP)

( * ) Notice: Subject to any disclaimer, the term of this patent is extended or adjusted under 35 U.S.C. 154(b) by 455 days.

(21) Appl. No.: 12/174,742

(22) Filed: Jul. 17, 2008

(65) Prior Publication Data

US 2009/0054822 A1    Feb. 26, 2009

(30) Foreign Application Priority Data

Aug. 22, 2007   (JP) .................................. 2007-215540

(51) Int. Cl.
*C02F 1/44* (2006.01)
*A61M 37/00* (2006.01)

(52) U.S. Cl. ..................... 604/6.09; 604/5.01; 604/5.04; 604/6.1; 604/6.11; 210/645; 210/646

(58) Field of Classification Search ................. 604/4.01, 604/5.01, 5.04, 6.09, 6.1, 6.11; 210/645, 210/646, 433.1

See application file for complete search history.

(56) References Cited

U.S. PATENT DOCUMENTS

| | | | |
|---|---|---|---|
| 5,866,015 A | 2/1999 | Kramer | |
| 6,153,109 A | 11/2000 | Krivitski | |
| 6,648,845 B1 | 11/2003 | Gotch et al. | |
| 2002/0128545 A1 | 9/2002 | Steuer et al. | |
| 2004/0073153 A1 | 4/2004 | Bosetto et al. | |
| 2004/0129616 A1 | 7/2004 | Mori et al. | |
| 2006/0043007 A1 | 3/2006 | Tarumi et al. | |
| 2006/0064025 A1 | 3/2006 | Kraemer | |
| 2007/0083145 A1 | 4/2007 | Murakami et al. | |
| 2009/0054822 A1 | 2/2009 | Murakami et al. | |

FOREIGN PATENT DOCUMENTS

| | | |
|---|---|---|
| JP | 9-173444 A | 7/1997 |
| JP | 2000-502940 A | 3/2000 |
| JP | 2001-502590 A | 2/2001 |
| WO | WO-98/32477 A1 | 7/1998 |
| WO | WO-02/053212 A1 | 7/2002 |

*Primary Examiner* — Leslie R Deak
(74) *Attorney, Agent, or Firm* — McDermott Will & Emery LLP

(57) ABSTRACT

A blood purification apparatus that can make the specific peak to be imparted to the blood more distinct, and therefore can detect blood recirculation reliably and precisely, is presented. It contains a blood circuit route, a blood pump, a dialyzer, dialysate introduction and discharge lines, a duplex pump, a pressurizing pump, a blood concentration means, and detection means that detect the specific peak imparted by the blood concentration means. The blood concentration means is configured to have an atmosphere release line, the tip of which is open to the atmosphere, that extends from between the pressurizing pump and the duplex pump in the dialysate discharge line, and to have an electromagnetic valve that can open or close the atmosphere release line. The electromagnetic valve opens the atmosphere release line to impart the specific peak by rapidly concentrating the blood flowing in the dialyzer for a short period of time.

10 Claims, 2 Drawing Sheets

US 7,931,610 B2

BLOOD PURIFICATION APPARATUS

CROSS-REFERENCE TO PRIOR RELATED APPLICATIONS

The present application claims priority under 35 U.S.C. §119 from Japanese Patent Application No. 2007-215540, filed on Aug. 22, 2007. The content of the Japanese application is incorporated by reference herein in its entirety.

FIELD OF THE INVENTION

The present invention is related to a blood purification apparatus that purifies while extracorporeally circulating the blood of a patient.

BACKGROUND OF THE INVENTION

Generally, blood purification therapy, for example, dialysis therapy, uses a blood circuit containing a flexible tube to circulate the blood of the patient extracorporeally. This blood circuit mainly contains an arterial blood circuit with an arterial needle installed on the end that collects blood from the patient, and a venous blood circuit with a venous needle installed on the end that returns blood to the patient; and the blood circulating extracorporeally is purified by interposing a dialyzer between these arterial blood and venous blood circuits.

The dialyzer is constituted such that multiple hollow fibers are arranged inside; the blood passes through the interiors of these hollow fibers, and dialysate can flow on the outside (between the outer surfaces of the hollow fibers and the inner surface of the chassis). The hollow fibers have micro-holes (pores) in the wall surfaces to form a blood purification membrane, and blood waste materials and the like that pass through the interior of the hollow fibers pass through the blood purification membrane and are discharged into the dialysate while the blood which has been purified by eliminating the waste materials is returned to inside the body of the patient. A water removal pump to remove water from the blood of the patient is arranged inside the dialysis apparatus so that water is removed during dialysis therapy.

In this regard, for example, when the arterial needle and the venous needle are inserted in and around the shunt (a part in which an artery and a vein are surgically connected) and circulation extracorporeally is performed, blood recirculation may occur in which the blood that has been purified and returned into the body of the patient from the venous needle in question, is re-introduced from the arterial needle without passing through the organs and the like of the patient. If this kind of blood recirculation occurs, the purified blood is circulated extracorporeally once again and the volume of blood requiring purification that is circulating extracorporeally is reduced by that amount, leading to the problem that the blood purification efficiency is reduced.

Nonetheless, in the past a dialysis apparatus was proposed that, by rapidly driving the water removal pump for a short period of time only, imparted a specific peak to change the blood concentration circulating extracorporeally, and extracorporeal blood recirculation could be detected by using this peak as a marker (see, for example, Japanese Patent Application Publication No. 2000-502940). According to the dialysis apparatus disclosed in this patent document, a sensor to detect the blood concentration (sensor to detect the hemoglobin concentration) was arranged in the arterial blood circuit, and blood recirculation during dialysis therapy was detected by using this sensor to detect the specific peak.

SUMMARY OF THE INVENTION

Nonetheless, in the aforementioned conventional blood purification apparatus there were the following kinds of problems because a specific peak was imparted to change the concentration of the blood circulating extracorporeally by driving the water removal pump rapidly for a short period of time only. Specifically, the water removal pump is normally set to drive at about 0.5 to 1.0 (L/H), and imparting a specific peak to the blood concentration by rapidly driving for a short period of time is not presupposed. Consequently, when imparting a specific peak using the water removal pump as in the past, the problem arises that this specific peak turns out indistinct and detection by the detection means can become difficult.

With the foregoing in view, the present invention provides a blood purification apparatus that can make the specific peak to be imparted to the blood distinct, and that can accurately and precisely detect blood recirculation.

An aspect of the present invention is a blood purification apparatus containing: a blood circuit route having an arterial blood circuit route and a venous blood circuit route to circulate extracorporeally the blood collected from a patient; a blood pump provided in the aforementioned arterial blood circuit route; a blood purification means that is connected between the aforementioned arterial blood circuit route and the aforementioned venous blood circuit route, and that purifies the blood flowing in the aforementioned blood circuit route; dialysate introduction and dialysate discharge lines that are connected to the aforementioned purification means; a dialysate introduction and discharge means that straddles the aforementioned dialysate introduction and dialysate discharge lines for the purposes of introducing dialysate from the aforementioned dialysis introduction line to the aforementioned blood purification means, and of discharging from the aforementioned dialysate discharge line the dialysate introduced into the aforementioned blood purification means; a pressurizing pump that is connected to the aforementioned dialysate discharge line between the aforementioned blood purification means and dialysate introduction and discharge means, and that causes dialysate to flow from the aforementioned blood purification means into the dialysate introduction and discharge means; a blood concentration means that can impart a specific peak to change the blood concentration; and a detection means to detect the specific peak imparted by the aforementioned blood concentration means; wherein the aforementioned blood concentration means has an atmosphere release line, the tip of which is open to the atmosphere, that extends from between the aforementioned pressurizing pump and the aforementioned dialysate introduction and discharge means in the aforementioned dialysate discharge line, and has a valve means that can open or close the aforementioned atmosphere release line; and the aforementioned blood concentration means imparts the aforementioned specific peak by rapidly concentrating the blood flowing in the aforementioned blood purification means for a short period of time.

Another aspect of the invention is the blood purification apparatus described above, wherein recirculated blood, in which blood returned to the patient from the aforementioned venous blood circuit is reintroduced and flows into the aforementioned arterial blood circuit, can be detected based on the specific peak detected by the aforementioned detection means.

A further aspect of the invention is the blood purification apparatus described above, wherein a bubble isolation chamber of a specified volume is connected to the aforementioned dialysate discharge line between the aforementioned pressurizing pump and the aforementioned dialysate introduction and discharge means, and the aforementioned atmosphere release line is extended from the aforementioned bubble isolation chamber.

A further aspect of the invention is the blood purification apparatus described above, wherein the aforementioned detection means contains a first detection means provided in the aforementioned arterial blood circuit, and a second detection means provided in the aforementioned venous blood circuit.

A further aspect of the invention is the blood purification apparatus described above, wherein a calculation means is provided that compares the specific peaks detected by the aforementioned first and second detection means, and that can calculate the percentage of recirculated blood in the blood that flows in the aforementioned arterial blood circuit.

A further aspect of the invention is the blood purification apparatus described above, wherein the aforementioned first and second detection means contain hematocrit sensors that detect the hematocrit levels in the blood circulating in the aforementioned arterial blood circuit and the aforementioned venous blood circuit.

A further aspect of the invention is the blood purification apparatus described above, wherein the release time of the aforementioned atmosphere release line using the aforementioned valve means can be optionally set to 10 seconds or less.

A further aspect of the invention is the blood purification apparatus described above, wherein the release time of the aforementioned atmosphere release line using the aforementioned valve means is automatically controlled to the optimum based on blood concentration information or pressure information.

A further aspect of the invention is the blood purification apparatus described above, wherein the rotational speed of the aforementioned pressurizing pump can be optionally varied when opening the aforementioned atmosphere release line using the aforementioned valve means.

A further aspect of the invention is the blood purification apparatus described above, wherein a warning device such as a dialysate pressure alarm, venous pressure alarm or dialyzer inlet pressure alarm is provided, and the alarm width of the alarm device is broadened only for a fixed time from the time of releasing the aforementioned atmosphere release line using the aforementioned valve means, or the alarm monitoring by the alarm device is relaxed only for a fixed time from the time of releasing the aforementioned atmosphere release line using the aforementioned valve means.

According to an aspect of the present invention, a specific peak is imparted by rapidly concentrating the blood flowing in the blood purification means for a short period of time by using the valve means to open the atmosphere release line, and therefore, the specific peak to be imparted to the blood can be made distinct in a shorter time, and the parameters related to the patient's blood access can be reliably and precisely detected.

According to another aspect of the invention, the specific peak to be imparted to the blood can be made distinct in a shorter time, and blood recirculation can be detected reliably and precisely.

According to a further aspect of the invention, a bubble isolation chamber of a specified volume is connected to the aforementioned dialysate discharge line between the aforementioned pressurizing pump and dialysate introduction and discharge means, and the aforementioned atmosphere release line is extended from the aforementioned bubble isolation chamber, and therefore the present invention can be applied by adapting the existing dialysis apparatus.

According to a further aspect of the invention, the detection means contains a first detection means provided in the arterial blood circuit and a second detection means provided in the venous blood circuit, and therefore, whether or not a specific peak has been imparted by the blood concentration means can be confirmed, the parameters when deriving the percentage of recirculated blood can be reduced, and blood recirculation can be reliably and accurately detected.

According to a further aspect of the invention, a calculation means is provided that compares the specific peaks detected by the first and second detection means, and that can calculate the percentage of recirculated blood in the blood that flows in the arterial blood circuit, and therefore, the error can be reduced and blood recirculation can be more precisely detected compared to devices that derive the percentage of recirculated blood based on other parameters such as the blood flow rate or water removal flow rate.

According to a further aspect of the invention, the first and second detection means contain hematocrit sensors that detect the hematocrit levels in the blood flowing in the arterial blood circuit and venous blood circuit, and therefore, the specific peak can be better detected.

According to a further aspect of the invention, the release time of the atmosphere release line using the valve means can be optionally set to 10 seconds or less, and therefore, the device can have sufficient measurement precision in a short period of time.

According to a further aspect of the invention, the release time of the atmosphere release line using the valve means is automatically controlled to the optimum based on blood concentration information or pressure information, and therefore, the parameters relating to the patient's blood access can be more precisely and reliably detected.

According to a further aspect of the invention, the rotational speed of the pressurizing pump can be optionally varied when opening the atmosphere release line using the valve means, and therefore, the degree of the negative pressure to be imparted can be controlled.

According to a further aspect of the invention, a warning device such as a dialysate pressure alarm, venous pressure alarm or dialyzer inlet pressure alarm is provided, and the alarm range based on the alarm device is broadened only for a fixed time from the time of releasing the atmosphere release line using the valve means, or the alarm monitoring based on the alarm device is relaxed only for a fixed time from the time of releasing the atmosphere release line using the valve means, and therefore, false alarms can be suppressed.

DETAILED DESCRIPTION OF THE INVENTION

Embodiments of the present invention will be concretely explained below with reference to the drawings.

Figure 1:
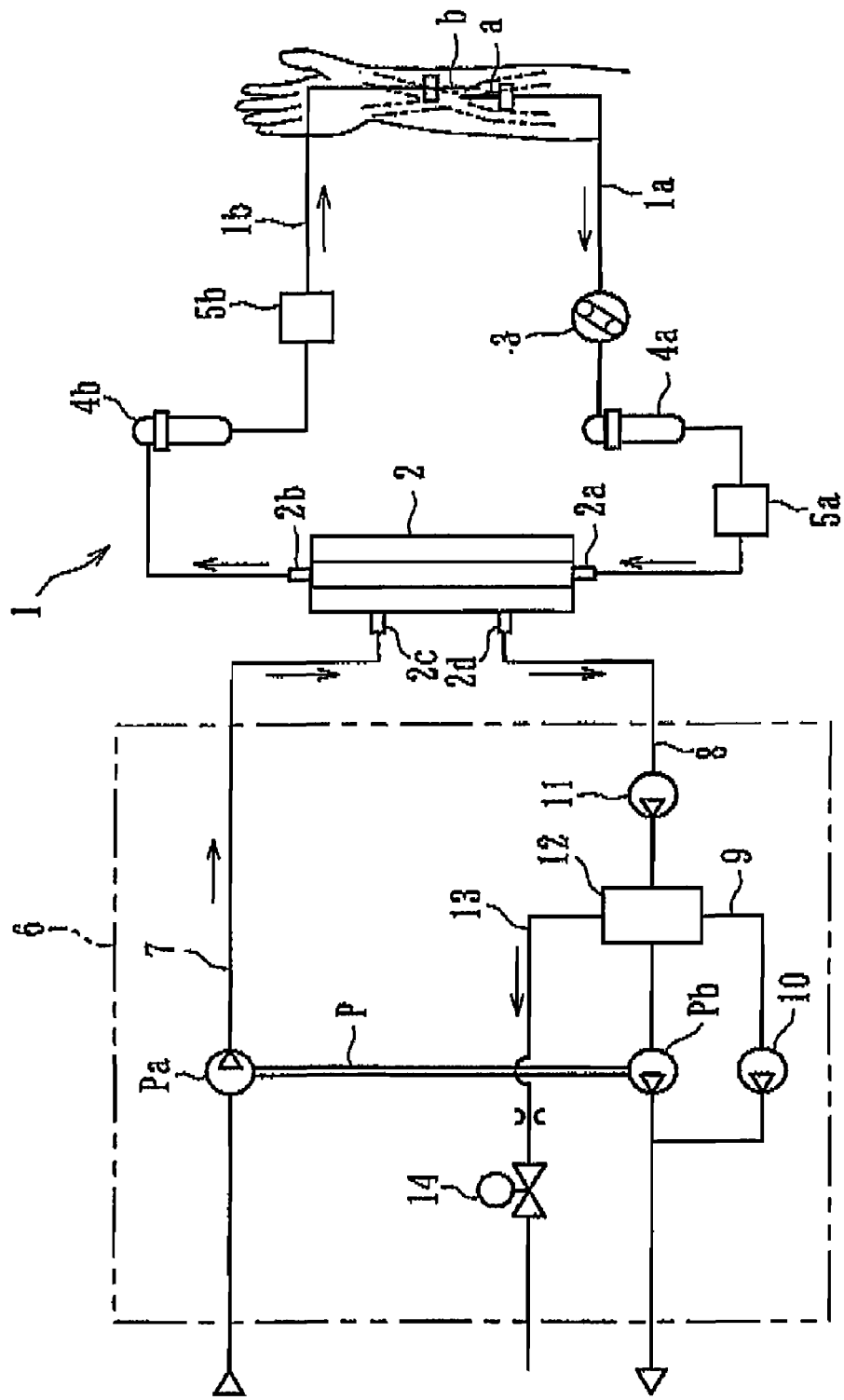
FIG. 1 is a full schematic diagram showing a blood purification apparatus related to an embodiment of the present invention.

The blood purification apparatus related to the present embodiment is for the purpose of purifying the blood of the patient during extracorporeal circulation, and is used in hemodialysis apparatuses for hemodialysis therapy. As indicated in FIG. 1, the hemodialysis apparatus mainly contains a blood circuit 1 to which a dialyzer 2 is connected as the blood purification means, and a dialysis apparatus main unit 6 that removes water while supplying dialysate to the dialyzer 2.

The blood circuit 1, as indicated in the same diagram, mainly contains an arterial blood circuit 1a and a venous blood circuit 1b made of flexible tubes, and the dialyzer 2 is connected between the arterial blood circuit 1a and the venous blood circuit 1b. An arterial needle a is connected to the tip of the arterial blood circuit 1a, and arranged midway are a peristaltic pump 3, a drip chamber 4a for removing bubbles, and a first detection means 5a. Meanwhile, a venous needle b is connected to the tip of the venous blood circuit 1b, and connected midway are a second detection means 5b and a drip chamber 4b for removing bubbles.

Then, with the arterial needle a and venous needle b inserted in the patient, when driving the blood pump 3, the blood of the patient arrives at the dialyzer 2 through the arterial blood circuit 1a while bubbles are removed by the drip chamber 4a, is purified by the dialyzer 2, and is returned into the body of the patient through the venous blood circuit 1b while bubbles are removed by the drip chamber 4b. Specifically, the blood of the patient is purified by the dialyzer 2 while being circulated extracorporeally by blood circuit 1.

A blood inlet 2a, a blood outlet 2b, a dialysate inlet 2c, and a dialysate outlet 2d are formed in the chassis of the dialyzer 2, and the terminal of the arterial blood circuit 1a is connected to the blood inlet 2a, and the terminal of the venous blood circuit 1b is connected to the blood outlet 2b. In addition, the dialysate inlet 2c and the dialysate outlet 2d are connected respectively to the dialysate introduction line 7 and the dialysate discharge line 8 extending from the dialysis apparatus main unit 6.

Multiple hollow fibers are housed inside the dialyzer 2; the interior of these hollow fibers makes up the blood flow route, and the dialysate flow route is between the outer surfaces of the hollow fibers and the interior surface of the chassis. A hollow fiber membrane is made by forming multiple microholes (pores) that pass through between the outer and interior surfaces of the hollow fibers, and is configured such that impurities and the like in the blood can permeate into dialysate through the membrane.

Meanwhile, the dialysis apparatus main unit 6 mainly contains a duplex pump P (dialysate introduction and discharge means), a bypass line 9 that is connected to the dialysate discharge line 8 and bypasses the duplex pump P, a water removal pump 10 connected to this bypass line 9, a pressurizing pump 11 that causes the dialysate to flow from the dialyzer 2 into the discharge side Pb of the duplex pump P, a bubble isolation chamber 12, an atmosphere release line 13, and an electromagnetic valve 14 (valve means).

The duplex pump P straddles the dialysate introduction line 7 and dialysate discharge line 8, and is for the purpose of introducing dialysate from the dialysate introduction line 7 into the dialyzer 2 (blood purification means), and of discharging from the dialysate discharge line 8 the dialysate introduced into the dialyzer 2. Specifically, the duplex pump P contains a volumetric pump in which the supply side Pa and the discharge side Pb have approximately the same volume, and with the electromagnetic valve 14 closed, the dialysate flow route from this supply side Pa to the discharge side Pb is a closed system (maintained in a closed state).

The pressurizing pump 11 is connected to the dialyzer discharge line 8 between the dialyzer 2 and the duplex pump P, is for causing the dialysate to flow from this dialyzer 2 to the duplex pump P, and contains a non-volumetric pump (pressure control type) such as a centrifugal type pump.

Then, one end of the dialysate introduction line 7 is connected to the dialyzer 2 (dialysate inlet 2c), and the other end is connected to the dialysate supply apparatus (not indicated in the diagram) that prepares dialysate of a specified concentration. Moreover, one end of the dialysate discharge line 8 is connected to the dialyzer 2 (dialysate outlet 2d), and the other end is connected to a fluid discharge means not indicated in the diagram. After being supplied from the dialysate supply apparatus and arriving at the dialyzer 2 through the dialysate introduction line 7, the dialysate is sent to the fluid discharge means through the dialysate discharge line 8 and the bypass line 9.

The water removal pump 10 is for the purpose of removing water from the blood of the patient that is flowing in the dialyzer 2. Specifically, when the water removal pump 10 is driven, because the duplex pump P is a volumetric pump, the volume of fluid discharged from the dialysate discharge line 8 is greater than the volume of dialysate introduced from the dialysate introduction line 7, and the amount of water removed from the blood is equivalent to that extra volume. Further, water may be removed from the blood of the patient by a means other than the water removal pump 10 (for example, by a device that utilizes a so-called balancing chamber or the like).

The bubble isolation chamber 12 is a so-called degassing chamber, having a specific volume and connected to the dialysate discharge line 8 between the pressurizing pump 11 and the duplex pump P, and is configured to be able to capture gas bubbles in the dialysate. The previously described bypass line 9 and the atmosphere release line 13 extend from this bubble isolation chamber 12. The tip of this atmosphere release line 13 is open to the atmosphere, and the electromagnetic valve 14 is connected midway as a valve means.

The electromagnetic valve 14 can open or close in order to open or close the atmosphere release line 13, and when it is open, the bubble isolation chamber 12 is linked to the outside air, and when it is closed, the bubble isolation chamber 12 is blocked from the outside air. However, if the electromagnetic valve 14 is operated so as to open the atmosphere release line 13 prior to dialysis therapy or after dialysis therapy, the gas bubbles captured inside the bubble isolation chamber 12 can be released to the atmosphere.

Here, the atmosphere release line 13 and the electromagnetic valve 14, the valve means, constitute the blood concentration means of the present invention, and by operating the electromagnetic valve 14 to open the atmosphere release line 13, the blood flowing in the dialyzer 2 can be rapidly concentrated for a short period of time and can be imparted with a specific peak. Specifically, during dialysis therapy, when the closed atmosphere release line 13 is opened by operating the electromagnetic valve 14, high negative pressure is instantly generated upstream of the pressurizing pump 11 because the outlet pressure of the pressurizing pump 11 is approximately equalized to atmospheric pressure, and water is rapidly removed (blood concentration) from the blood flowing in the dialyzer 2 (blood flow route) for a short period of time.

The pressure is thereby far greater than the ultrafiltration pressure generated by driving the water removal pump 10, and a large volume of water can be removed from the blood for a short period of time, allowing a specific peak to be imparted to change the blood concentration (hematocrit level). Further, by using the electromagnetic valve 14, the atmosphere release line 13 is opened for a short time (in the present embodiment, the opening of the atmosphere release line 13 can be set for an optional time of 10 seconds or less, and there is sufficient precision of measurement when opening for just 1 second), and then the atmosphere release line 13 is closed immediately by operating the electromagnetic valve 14. The duration that the atmosphere release line 13 is opened by this electromagnetic valve 14 is based on blood concentration information (information relating to the concentration of the patient's blood), or on pressure information (venous pressure or dialysate pressure, and the like), and preferably is automatically controlled to the optimal level. Here, "rapidly and for a short period of time" in the present invention means a large enough size and time that the imparted pulse can be confirmed after passing through the circuit; and "specific" means a peak that can be distinguished from a fluctuation of the pump, from a movement of the body of the patient, or from a fluctuation pattern based on other factors. In addition, the water removal speed based on the present embodiment is 10 times or more that of normal water removal.

The blood concentration information of the patient may be the blood concentration of the patient (hematocrit level or hemoglobin concentration, etc.), or information derived from the venous pressure, which is the blood pressure flowing in the venous blood circuit 1b (for example, the venous pressure calculated from the pressure of the air layer of the drip chamber 4b), or the dialysate pressure, which is the pressure of dialysate discharged from the dialyzer 2 (fluid pressure of the dialysate in the dialysate discharge line 8 immediately after the dialyzer 2).

Further, it is preferable to be able to optionally vary the rotational speed of the pressurizing pump 11 when using the electromagnetic valve 14 to open the atmosphere release line 13. The degree of the negative pressure imparted can thereby be controlled. Moreover, if the apparatus is configured so that a warning device such as a dialysate pressure alarm, venous pressure alarm or dialyzer inlet pressure alarm is provided, false alarms can be suppressed by broadening the alarm width (alarm range) of the alarm device only for a fixed time from the time of opening the atmosphere release line 13 using the electromagnetic valve 14. In order to further suppress alarms, the apparatus may be configured such that alarm monitoring by the alarm device is relaxed only for a fixed time from the time of releasing the aforementioned atmosphere release line 13 using the valve means 14.

The first detection means 5a and the second detection means 5b are arranged in the arterial blood route 1a and the venous blood route 1b respectively, and detect the concentration (concretely, the hematocrit level) of the blood flowing in these circuits. These detection circuits 5a and 5b contain hematocrit sensors, and the hematocrit sensors provide, for example, a light emitting element such as an LED and a photoreceptive element such as a photodiode. The hematocrit level, which indicates the blood concentration of the patient, is detected by using the light emitting element to irradiate the blood with light, and using the photoreceptive element to receive the light that passes through or the light that is reflected.

Concretely, the hematocrit level, which indicates the blood concentration, is calculated based on electric signals output from the photoreceptive element. Specifically, the various components of the erythrocytes and plasma that constitute blood have unique light absorbance characteristics, respectively, and by using these characteristics, the hematocrit level in question can be calculated by optoelectronically quantifying the erythrocytes necessary in order to measure the hematocrit level More concretely, near infrared rays irradiated from the light emitting element incident on the blood are affected by absorption and diffusion, and the light is received by the photoreceptive element. The hematocrit level is calculated by analyzing the percentages of absorption and diffusion of the light from the strength of the light received.

The first detection means 5a constituted as described above is arranged in the arterial blood circuit 1a, and therefore the hematocrit level of the blood collected from the patient through the arterial needle a during dialysis therapy is detected; and the second detection means 5b is arranged in the venous blood circuit 1b, and therefore the hematocrit level of the blood purified by the dialyzer 2 and returned to the patient is detected. Specifically, the specific peak imparted by opening the electromagnetic valve 14 is first detected by the second detection means 5b, and afterwards if that blood arrives once again at the arterial blood circuit 1a and is recirculated, the first detection means 5a can detect the specific peak remaining in that recirculated blood (refer to FIG. 3).

The second detection means 5b can thereby confirm whether or not a specific peak was imparted by operating the electromagnetic valve 14 to open the atmosphere release line 13, and the first detection means 5a can detect the presence or absence of recirculation. Specifically, whether or not a specific peak has been imparted can be confirmed, and therefore, blood recirculation can be more reliably and precisely detected than when a detection means has been arranged only in the arterial blood circuit.

Figure 4:
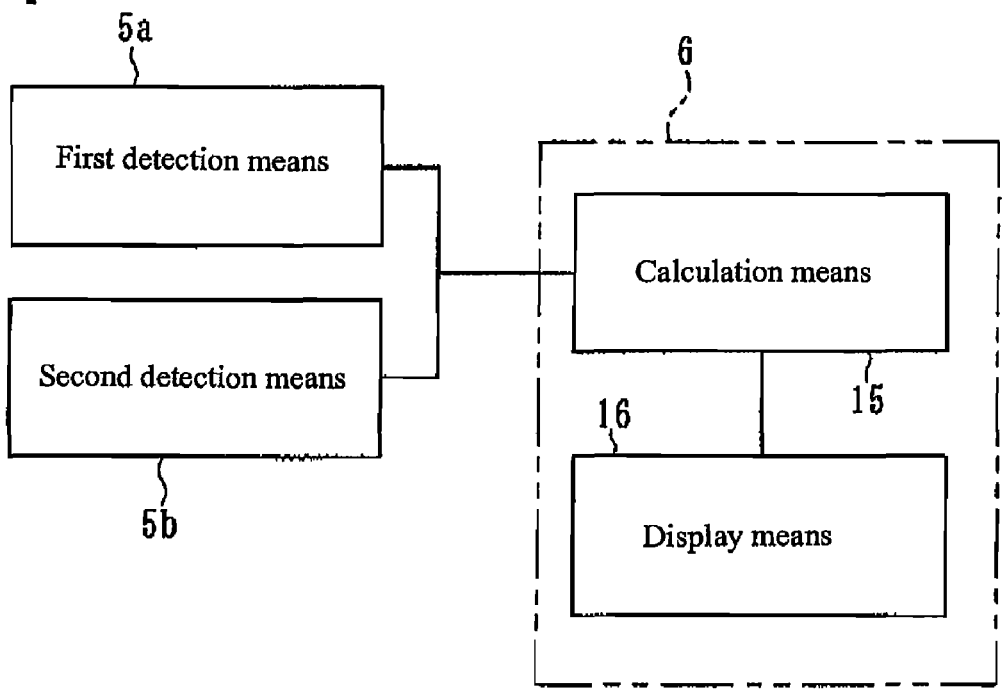
FIG. 4 is a block diagram showing the connection relationships of the first detection means, second detection means, calculation means, and display means of the same blood purification apparatus.

Further, as indicated in FIG. 4, the aforementioned first detection means 5a and second detection means 5b are electrically connected to a calculation means 15 that is arranged in the dialysis apparatus main unit 6, and this calculation means 15 is electrically connected to a display means 16 such as a liquid crystal display. The calculation means 15 is constituted, for example, by a microcomputer, and the percentage of recirculated blood in the blood flowing through the arterial blood circuit la can be calculated by comparing the hematocrit levels (specific peaks) detected by the first detection means 5a and the second detection means 5b.

Concretely, the time from imparting the specific peak until that blood arrives at the second detection means 5b (time t1 in FIG. 2) and the time until arriving at the first detection means 5a by recirculating (time t3 in FIG. 3) are estimated for when there is blood recirculation; and after imparting the specific peak, the calculation means 15 compares the hematocrit level detected by the second detection means 5b when time t1 has elapsed with the hematocrit level detected by the first detection means 5a when time t3 has elapsed.

In this way, by estimating the time t1 until the blood arrives at the second detection means 5b and the time t3 until the blood arrives at the first detection means 5a by recirculating, it is possible to distinguish cardiopulmonary recirculation (the phenomenon in which purified blood only passes through the heart and lungs, and is drawn outside the body without passing through the other tissues, organs and the like), and recirculation, which is the target measurement. Further, instead of the method in question, the calculation means 15 may be used to ascertain that the hematocrit levels detected by the first detection means 5a and the second detection means 5b exceeded specified numeric values, and the hematocrit levels that exceeded the numeric values may then be compared.

Figure 2:
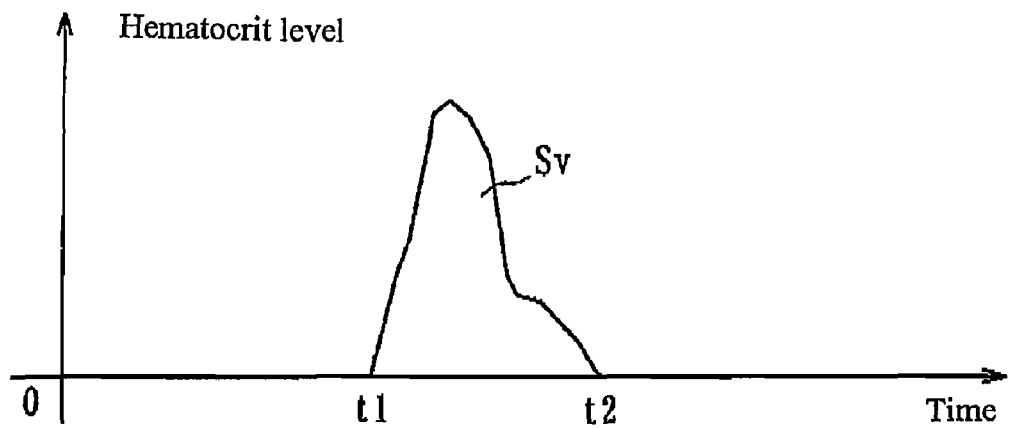
FIG. 2 is a graph showing changes in the hematocrit level detected by the second detection means of the same blood purification apparatus.
Figure 3:
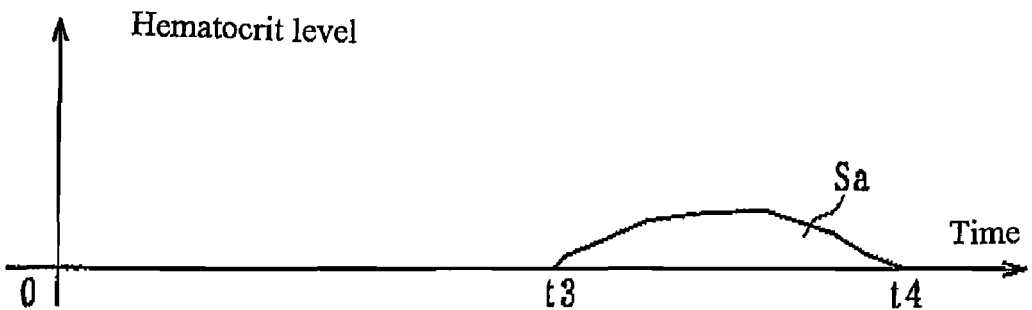
FIG. 3 is a graph showing changes in the hematocrit level (if there is recirculation) detected by the first detection means of the same blood purification apparatus.

Then, based on graphs of the time-hematocrit level like those indicated in FIGS. 2 and 3, the changes in hematocrit levels at the first detection means 5a and the second detection means 5b are derived, and the area of the part (changed part) of the elapsed time that is to be compared as described above, is calculated by using a mathematical method such as integration. For example, letting Sv be the area of the changed part (part from t1 to t2 in FIG. 2) at the second detection means 5b and letting Sa be the area of the changed part (part from t3 to t4 in FIG. 3) at the first detection means 5a, the percentage of recirculated blood (recirculation percentage) Rrec is derived by the following formula:

$$Rrec(\%)=Sa/Sv\times100.$$

Here, taking into consideration diffusion that takes place during the process of the blood imparted with the specific peak flowing from the second detection means 5b to the first detection means 5a, the time of the changed part at the first detection means 5a (time interval from t3 to t4) was set larger than the time of the changed part at the second detection means 5b (time interval from t1 to t2). The percentage of the calculated recirculated blood is displayed on the display means 16 arranged in the dialysis apparatus main unit 6 to enable monitoring by medical-related personnel such as physicians. Further, if no blood is recirculating, then the aforementioned Sa will be 0, and therefore the numerical value 0 (%) will be displayed as the percentage of recycled blood. In addition to the presence or absence of blood recirculation, the medical-related personnel can thereby become aware of that percentage, and this can be a reference for subsequent treatment (to take measures such as resetting the needle to suppress blood recirculation, reforming the shunt, or the like).

According to embodiments like the above, a specific peak is imparted by rapidly concentrating the blood flowing in the dialyzer 2, which is the blood purification means, for a short period of time by using the electromagnetic valve 14 as the valve means to open the atmosphere release line 13, and therefore, the specific peak to be imparted to the blood can be made distinct in a shorter time, and blood recirculation can be reliably and precisely detected. In addition, a bubble isolation chamber 12 of a specified volume is connected to the dialysate discharge line 8 between the aforementioned pressurizing pump 11 and the duplex pump P (dialysate introduction and discharge means), and the atmosphere release line 13 is extended from the bubble isolation chamber 12; consequently, the present invention can be applied by adapting an existing dialysis apparatus.

In addition, error can be reduced and blood recirculation can be detected more precisely compared to devices that calculate the percentage or recycled blood based on other parameters such as the blood flow rate or the water removal flow rate. Specifically, the blood flow rate and the water removal flow rate are generally derived from the drive velocity of the blood pump and the water removal pump, and therefore errors are prone to occur between the drive velocity and the actual flow rate. In contrast to an increase in error and deterioration of precision when calculating the percentage of recirculated blood using these as parameters, the present embodiment can suppress error because these flow rates are not used as parameters.

Further, the burden on the patient can be lightened because the blood concentration time and measurement time are short. Also, an existing circuit can be used unchanged without modifying the extracorporeal circulation circuit and the like, and blood recirculation can be detected during therapy. The effects on the therapy itself (lengthening of the dialysis time and the like) can be controlled and the effects on the patient (physical and psychological burdens) can be minimized by conducting this detection operation once during one dialysis treatment. Moreover, because it is not necessary to infuse an indicator (marker) or the like, admixture of impurities or infection arising from infusion from a port or the like can be prevented; and no indicator infusion port or infusion means are necessary because the marker for detecting blood recirculation is imparted by an existing dialyzer 2. Further, detection of blood recirculation can be automated, and operator-caused fluctuations of results during manual operation can be suppressed.

In addition, by using two detection means, namely the first detection means 5a and the second detection means 5b, the two detected values can be compared with no water removal in between, and automatic calibration is possible. Further, because the first detection means 5a and the second detection means 5b are arranged respectively in the inlet and outlet sides of the dialyzer 2, the water removal performance of the dialyzer 2 can be monitored.

Moreover, if the first detection means 5a and the second detection means 5b are configured as hematocrit sensors as in the present embodiment, the specific peak can be better detected and blood recirculation can be more precisely detected because the imparted specific peak clearly manifests as a change in hematocrit level. Further, as indicated in FIG. 1, the imparted specific peak can be detected more quickly because the second detection means 5b in the present embodiment is arranged near the dialyzer 2, and blood recirculation can be detected more precisely because there is little effect from blood diffusion.

The present embodiment was explained above, but the present invention is not limited to this, and for example, as long as the specific peak imparted rapidly and in a short time by water removal can be detected, the first detection means and the second detection means may be configured by sensors other then hematocrit sensors (for example, sensors that detect hemoglobin concentration, sensors that detect proteins, and the like). In addition, as long as the first detection means and the second detection means are in the arterial blood circuit and venous blood circuit respectively, they may be placed in any position. Further, the apparatus may be configured such that a detection means is arranged in either the arterial blood circuit or the venous blood circuit.

Moreover, in the present invention the bubble isolation chamber 12 of a specified capacity is connected to the dialysate discharge line 8 in between the pressurizing pump 11 and the duplex pump P, and the atmosphere release line 13 is extended from this bubble isolation chamber 12, but the atmosphere release line 13 need not be extended from the bubble isolation chamber 12 as long as it is extended from the dialysate discharge line 8 in between the pressurizing pump 11 and the duplex pump P (dialysate introduction and discharge means).

Further, in the present embodiment, the percentage of recirculation (recirculation percentage) is calculated by the calculation means, but a calculation means need not be provided, and the first detection means 5a may detect only the presence or absence of blood recirculation while the second detection means 5b confirms only whether or not a specific peak has been imparted. Further, the medical-related personnel may be warned by sounding an alarm or the like when the percentage of recirculated blood exceeds a specified numeric value. In the present embodiment the dialysis apparatus main unit 6 contains a dialysis monitoring device that does not have a built-in dialysate supply mechanism, but the present invention may be applied to an individual dialysis apparatus with a built-in dialysate supply mechanism.

Additionally, in the present invention, recirculated blood, in which blood returned to the patient from the venous blood circuit is re-introduced and flows into the arterial blood circuit, can be detected based on a specified peak detected by a detection means, but the present invention can also measure shunt flow rate or measure cardiac output. If a shunt has been used for many years, the vascular diameter may have changed by the onset of stenosis, thrombus or aneurism, making it difficult to guarantee the necessary amount of extracorporeal circulation for dialysis, and therefore, shunt management is important for satisfactory dialysis.

Currently, to confirm that the shunt of a dialysis patient is effectively used, the blood flow rate of the shunt is measured by auscultation of the blood flow sound at the shunt part using a stethoscope, by ultrasonography, by X-ray, or the like. One of these techniques is to infuse physiological saline into the extracorporeal blood circulation circuit, and to calculate the shunt flow rate by drawing a dilution curve. In this case, there are the disadvantages that labor is required and that the syringe and physiological saline must be individually prepared. According to the present embodiment, these issues can be resolved. For example, the following procedure is what is necessary to be able to measure the shunt flow rate.

First, the arterial needle a of the arterial blood circuit 1a and the venous needle b of the venous blood circuit 1b are inserted into the shunt of the patient such that they are mutually reversed from the state used during therapy (reverse insertion), creating a situation in which the recirculation percentage is 100%. In this state, when the electromagnetic valve 14 is operated and the atmosphere release line 13 is opened, a blood concentration clump is detected respectively by the first detection means 5a of the arterial blood circuit 1a and the second detection means 5b of the venous blood circuit 1b.

At this time, if the shunt flow rate (Qa)=the extracorporeal blood flow rate (Qb), then the areas (the area wherein the horizontal axis is time and the vertical axis is the blood concentration level as in FIGS. 2 and 3) of the concentration clumps detected by the first detection means 5a and the second detection means 5b are equal, and if the shunt flow rate (Qa) and the extracorporeal blood flow rate (Qb) are not equal, then the concentrated blood is diluted when returned into the shunt (shunt blood vesicle), and therefore a diluted blood clump is detected by the first detection means 5a of the arterial blood circuit 1a.

Additionally, the shunt flow rate can be calculated by comparing the area of the blood concentration clump detected by the first detection means 5a of the arterial blood circuit 1a and the area of the blood concentration clump detected by the second detection means 5b of the venous blood circuit 1b. Specifically, letting Sa be the area of the blood concentration clump detected by the first detection means 5a, and letting Sv be the area of the blood concentration clump detected by the second detection means 5b, the relational formula Sa:Sv=Qa+Qb:Qb is established. The shunt flow rate can thereby be calculated by solving for Qa=Qb×(Sv/Sa−1).

The blood concentration means is configured to have an atmosphere release line with an end open to the atmosphere, which is extended from the dialysate discharge line between the pressurizing pump and the dialysate introduction and discharge means, and to have a valve means that can open or close this atmosphere release line; and as long as it is a blood purification apparatus that imparts a specific peak by rapidly concentrating the blood that flows though the blood purification means for a short period of time by opening this valve means, the invention may be applied to devices used in other therapies (blood filtration therapy, blood filtration and hemodialysis therapy, and the like) that purify blood while conducting extracorporeal circulation, or to devices with other added functions.

What is claimed is:

1. A blood purification apparatus comprising:
    a blood circuit route having an arterial blood circuit route and a venous blood circuit route to circulate extracorporeally blood collected from a patient;
    a blood pump provided in said arterial blood circuit route;
    a blood purification device that is connected between said arterial blood circuit route and said venous blood circuit route, and purifies the blood flowing in said blood circuit route;
    dialysate introduction and dialysate discharge lines that are connected to said blood purification device;
    a dialysate introduction and discharge device that straddles said dialysate introduction and dialysate discharge lines for the purposes of introducing dialysate from said dialysate introduction line to said blood purification device; and of discharging from said dialysate discharge line the dialysate introduced into said blood purification device;
    a pressurizing pump that is connected to said dialysate discharge line between said blood purification device and said dialysate introduction and discharge device, and that causes dialysate to flow from said blood purification device into said dialysate introduction and discharge device;
    a blood concentration device is configured to impart a specific peak to change blood concentration; and
    a detection device configured to detect the specific peak imparted by said blood concentration device;
    wherein
    said blood concentration device comprises:
        an atmosphere release line, the tip of which is open to atmosphere, that extends from between said pressurizing pump and said dialysate introduction and discharge device in said dialysate discharge line; and
        a valve unit that can open or close said atmosphere release line; and
    said blood concentration device is configured to impart said specific peak by rapidly concentrating the blood flowing in said blood purification device for a short period of time.

2. The blood purification apparatus described in claim 1, wherein the detection device is configured to detect recirculated blood, in which blood returned to the patient from said venous blood circuit route is reintroduced and flows into said arterial blood circuit route, based on the specific peak detected by said detection device.

3. The blood purification apparatus described in claim 1, further comprising a bubble isolation chamber of a specified volume that is connected to said dialysate discharge line between said pressurizing pump and said dialysate introduction and discharge device, wherein said atmosphere release line is extended from said bubble isolation chamber.

4. The blood purification apparatus described in claim 1, wherein said detection device comprises a first detection unit provided in said arterial blood circuit route, and a second detection unit provided in said venous blood circuit route.

5. The blood purification apparatus described in claim 4, further comprising a calculation device that compares the specific peaks detected by said first and second detection units, and that can calculate the percentage of recirculated blood in the blood that flows in said arterial blood circuit route.

6. The blood purification apparatus described in claim 4, wherein said first and second detection units each comprise a hematocrit sensor that detects the hematocrit level in the blood circulating in said arterial blood circuit route and said venous blood circuit route, respectively.

7. The blood purification apparatus described in claim 1, wherein release time of said atmosphere release line using said valve unit can be optionally set to 10 seconds or less.

8. The blood purification apparatus described in claim 1, wherein release time of said atmosphere release line using said valve unit is automatically controlled to an optimum based on blood concentration information or pressure information.

9. The blood purification apparatus described in claim 1, wherein rotational speed of said pressurizing pump can be optionally varied when opening said atmosphere release line using said valve unit.

10. The blood purification apparatus described in claim 1, further comprising an alarm device, wherein an alarm width of the alarm device is broadened only for a fixed time from the time of releasing said atmosphere release line using said valve unit, or alarm monitoring by the alarm device is relaxed only for a fixed time from the time of releasing said atmosphere release line using said valve unit.

* * * * *